(12) United States Patent
Fry et al.

(10) Patent No.: US 7,987,693 B2
(45) Date of Patent: Aug. 2, 2011

(54) METHOD AND DEVICE FOR AUTOMATED ELECTRONIC GREEN SPEED MEASUREMENT

(76) Inventors: Steven Fry, Carlisle, PA (US); Eric Fry, Carlisle, PA (US)

( * ) Notice: Subject to any disclaimer, the term of this patent is extended or adjusted under 35 U.S.C. 154(b) by 503 days.

(21) Appl. No.: 12/288,263

(22) Filed: Oct. 17, 2008

(65) Prior Publication Data

US 2009/0100928 A1    Apr. 23, 2009

Related U.S. Application Data

(60) Provisional application No. 60/999,422, filed on Oct. 18, 2007.

(51) Int. Cl.
*G01N 3/56* (2006.01)
*A63B 57/00* (2006.01)

(52) U.S. Cl. .............................. 73/9; 473/404

(58) Field of Classification Search ......... 73/9; 473/404
See application file for complete search history.

(56) References Cited

U.S. PATENT DOCUMENTS

| | | | |
|---|---|---|---|
| 3,215,436 A * | 11/1965 | Carter | 473/171 |
| 5,067,718 A | 11/1991 | Knox | |
| 5,788,583 A | 8/1998 | Agulnek | |
| 6,547,680 B1 | 4/2003 | Marchese, Jr. | |
| 6,749,526 B2 * | 6/2004 | Hughes | 473/404 |
| 6,749,527 B2 * | 6/2004 | Hughes | 473/404 |
| 6,860,139 B2 * | 3/2005 | Pelz | 73/9 |
| 6,872,150 B2 | 3/2005 | Welch | |
| 7,220,187 B2 | 5/2007 | Schmidt | |
| 7,225,663 B2 * | 6/2007 | Pelz | 73/9 |
| 7,255,649 B1 | 8/2007 | McConnell | |
| 7,306,524 B1 * | 12/2007 | Rogers | 473/167 |
| 2003/0226393 A1 * | 12/2003 | Pelz | 73/9 |
| 2004/0058754 A1 * | 3/2004 | Hughes | 473/404 |
| 2004/0097303 A1 * | 5/2004 | Hughes | 473/404 |
| 2005/0145011 A1 * | 7/2005 | Pelz | 73/9 |
| 2006/0287119 A1 * | 12/2006 | Penner et al. | 473/131 |

* cited by examiner

*Primary Examiner* — Hezron Williams
*Assistant Examiner* — Nathaniel Kolb (57) ABSTRACT

Method and apparatus for measuring the coefficient of rolling friction or speed of a horizontal surface over which a round object is rolled such as a putting green encountered in the game of golf. The method includes a device for launching a ball across the surface at a constant and consistent velocity. An included timing device is triggered to start counting the elapsed time when the ball exits the launching device and continues counting until the ball has decelerated to a stop. At the instant the ball ceases moving the timer is triggered to terminate the count. The time required for a body with a specific velocity to come to rest after experiencing constant deceleration is determined by the laws of motion. The coefficient of friction or "speed" of the green which is proportional to the amount of deceleration may then be calculated. This time measurement is therefore sufficient to determine the speed of the green surface which may be reported as an equivalent "stimp" value.

8 Claims, 11 Drawing Sheets

METHOD AND DEVICE FOR AUTOMATED ELECTRONIC GREEN SPEED MEASUREMENT

CROSS-REFERENCE TO RELATED APPLICATIONS

This application claims the benefit of provisional patent application Ser. No. 60/999,422, filed 2007 Oct. 18 by the present inventor.

FEDERALLY SPONSORED RESEARCH

Not Applicable

SEQUENCE LISTING OR PROGRAM

Not Applicable

BACKGROUND

1. Field

This invention relates to a method and apparatus for measuring the coefficient of rolling friction or "speed" of a surface over which a spherical projectile is rolled such as would be encountered in the game of golf on the putting green. In particular, the present invention pertains to an electronic measurement of the relative speed of the surface by sensing the time to come to rest after the ball is launched at a known initial velocity.

2. Prior Art

It is well known that putting is an integral and critical part in playing the game of golf. Being able to judge the amount of force required to propel the golf ball the exact distance to reach the target hole is extremely important to successful putting and being able to post the best possible score. This amount of force required is determined by the distance to be traversed and the effective coefficient of rolling friction of the putting green surface. This is referred to as the "speed" of the green and is affected by many factors such as the length and condition of the grass and the moisture content.

A device for measuring the speed of a putting green was developed by Edward Stimpson in 1937. This instrument which has become known as a stimpmeter consists of a ramp which releases a ball from a specific height at a predetermined angle from the horizontal. This effectively launches the ball across the green surface at a constant initial velocity. The distance that the ball rolls before coming to rest is proportional to the coefficient of rolling friction or the speed of the green. The length of the Stimpmeter from the ball release position to the release end is 30 inches. The ball is released when the ramp has been elevated to an angle of 20 degrees. The amount of kinetic energy imparted to the ball therefore results in an initial velocity of approximately 95 inches per second as the ball leaves the ramp. The distance, measured in feet, that the ball rolls across the green given this velocity has been defined as the "stimp value" of the green. The stimpmeter has been designated by the U.S. Golf Association as the recognized standard for measuring and categorizing putting green speeds. This distance may vary between approximately 6 feet for a very slow green to 14 feet for a fast green. This system of measurement has become the de-facto standard for classifying the speed of a putting green.

Although there have been some incremental improvements in this measurement device over the years, the basic method has not changed since its inception some seventy years ago. A similar apparatus was developed by David Pelz as described in U.S. Pat. No. 6,860,139. Pelz's contribution to the art was to design a precision version of the original stimpmeter that eliminated some of the variables that could contribute to inconsistencies in the reading, such as instability in holding the ramp steady during the release and variations in the exact height of the ball at the time of release. Another device disclosed by Marchese in U.S. Pat. No. 6,547,680 is basically a replica of the original stimpmeter with a few embellishments. Other prior art includes U.S. Pat. No. 6,749,527 to Hughes. This invention is a scaled down, collapsible version of the stimpmeter ramp. One common characteristic of these prior art methods is the requirement that a physical distance measurement be taken to determine the length of the path that the ball has rolled after being released from the device. This action is relatively time consuming and inconvenient for frequent or casual use in the characterization of putting surfaces. An electronic apparatus which does not require a measurement of the distance rolled is disclosed in U.S. Pat. No. 7,306,524 to Rogers. The change in velocity or deceleration that occurs between two points on the surface to be measured is used to calculate the speed of the green. This device is relatively large and bulky and not well suited to casual or frequent use on the course.

All of the devices and methods heretofore known suffer from one or more disadvantages when compared to the present invention:

(a) A physical measurement of the distance rolled by the measuring ball across the green must be performed by the operator using a tape measure or similar instrument. This action is relatively time consuming and inconvenient to complete.

(b) The devices are too large to be routinely carried for repeated and frequent use throughout the course of play.

SUMMARY

In accordance with one embodiment the present invention provides a new method and device which rapidly and conveniently produces an accurate measure of the coefficient of rolling friction or relative speed of a surface across which a ball is rolled such as a golf green. This device offers major advantages over devices of prior art designed for a similar purpose addressing the foregoing concerns.

Accordingly, it is an object of this invention to remove the requirement of most prior art where it is necessary to physically measure the distance traveled by the rolling ball using a tape measure or similar length measuring instrument. It is a further object of the present invention to provide a means for quickly determining the green speed of the current putting surface utilizing a single device without requiring a physical measurement on the green. It is also an object of the invention to make a green speed evaluation so convenient that it takes less time and effort than is typically spent lining up a putt and reading the break of the green surface. It is a further object of the invention to provide a compact hand held device that can be unobtrusively attached to a belt or golf bag for ease of use. The present invention disclosed herein achieves all of these objectives.

The accompanying drawings which support the description in the specification illustrate this new method for green speed measurement and several embodiments demonstrating the principles of the invention.

DRAWINGS

Figures

In the drawings, closely related figures have the same number but different alphabetic suffixes.

DRAWINGS

Reference Numerals

| | |
|---|---|
| 12 | measuring ball |
| 14 | ramp |
| 15 | horizontal surface |
| 16 | initial position |
| 18 | final position |
| 20 | timer start sensor |
| 22 | timer stop sensor |
| 23 | time base |
| 24 | timer |
| 26 | central processing unit |
| 28 | numerical display |
| 30 | ball rail |
| 32 | vertical ball rail support |
| 34 | stabilizing cross member |
| 38 | electronic timing and control module |
| 40 | spacing block |
| 41 | start switch |
| 42 | stop switch |
| 44 | numeric display |
| 46 | electronic timing circuit |
| 47 | time base |
| 48 | central processing unit (CPU) |
| 49 | wireless receiver circuit |
| 50 | hand held body |
| 54 | ball plunger shaft |
| 56 | bushing bearing |

-continued

| | |
|---|---|
| 58 | ball contact pad |
| 60 | retaining washer |
| 62 | retention notch |
| 64 | compression spring |
| 66 | retention bracket |
| 68 | conical spring |
| 70 | back plug |
| 72 | launch cavity |
| 74 | rear release cavity |
| 76 | retention bracket slot |
| 78 | electronic timing and control circuit |
| 79 | stop switch |
| 80 | wireless motion sensing ball |
| 82 | start switch |
| 83 | angular rate sensor |
| 84 | wireless transmitting circuit |
| 86 | alignment pins |
| 88 | battery |
| 90 | battery cavity |

DETAILED DESCRIPTION

Figure 1:
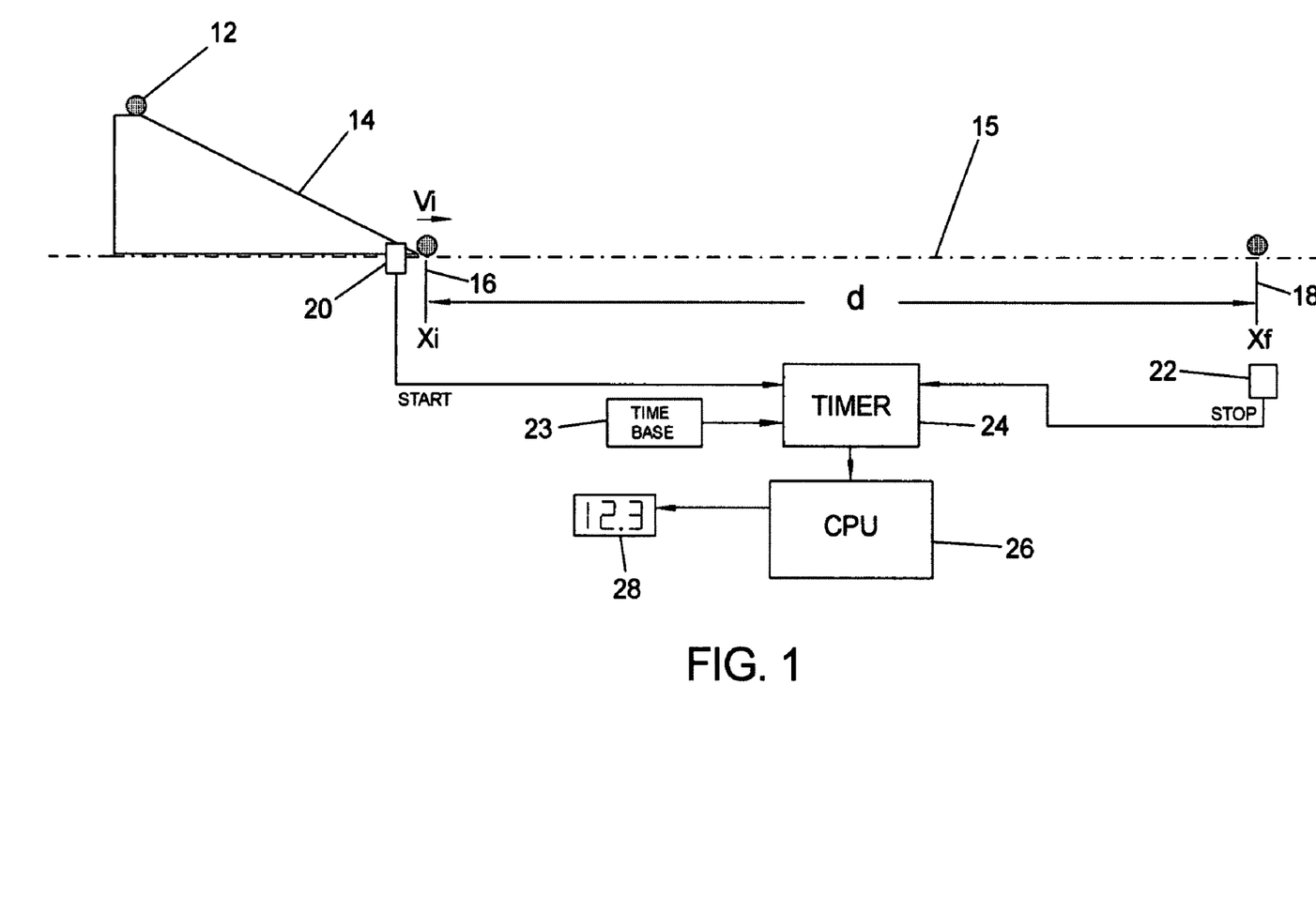
FIG. 1 shows a conceptual diagram illustrating the important elements and method of operation of the invention.

FIG. 1—First Embodiment

Reference will now be made to the drawings to demonstrate and teach the method of the invention and provide detailed descriptions of several operational embodiments which implement the technique.

Referring to FIG. 1, feature 15 indicates a substantially horizontal surface of which it is desired to characterize and quantize the coefficient of rolling friction or effective green speed if the surface is a golf putting green. Measuring ball 12 is projected across the surface to enable the measurement. A means for launching the ball across the horizontal surface 15 at a substantially constant and repeatable initial velocity is provided by item 14, in this instance being implemented as a fixed height ramp. A timer start sensor 20 provides a signal which starts the timer counting the elapsed time when the ball is released from the end of the ramp 14. The ball then rolls across surface 15 with decreasing velocity until all of the kinetic energy has been dissipated by the friction of the green. A signal is generated by a timer stop sensor 22 at the instant that the ball 12 stops rolling and comes to rest. Timer 24 measures the elapsed time required for the ball 12 to traverse from its initial position $X_i$ 16 until it comes to a complete stop at its final position at $X_f$ 18. The accuracy of the timing measurement is assured by reference to precision time base 23. The stop signal generated by sensor 22 stops the counter which subsequently contains the time required for the ball to traverse the horizontal surface 15 from the base of the ramp at initial position $X_i$ 16 until reaching its resting point at final position $X_f$ 18. Central Processing Unit 26 receives the result of the timing measurement and calculates the equivalent coefficient of friction or green speed of the surface 15. The result of this computation is then communicated to a numerical display device 28 which reports the results of the measurement to the operator.

It is a known physical observable fact that an object in motion which is under the influence of negative acceleration or deceleration will eventually cease moving and come to rest. The time required to come to rest is directly proportional to the initial velocity of the body and the amount of negative acceleration. This deceleration is directly proportional to the coefficient of friction in the case of a sliding or rolling object. In the case where the initial velocity is a known quantity, the elapsed rolling time will be primarily dependent on the coefficient of friction of the sliding surface. This quantity may be converted to an equivalent distance traveled, d. When measured in feet, this rolling distance is defined as the "stimp" value of the golf green. This distance vs. rolling time may be predicted using an algebraic formula, but should be verified and calibrated for specific embodiments with empirical data.

Figure 2:
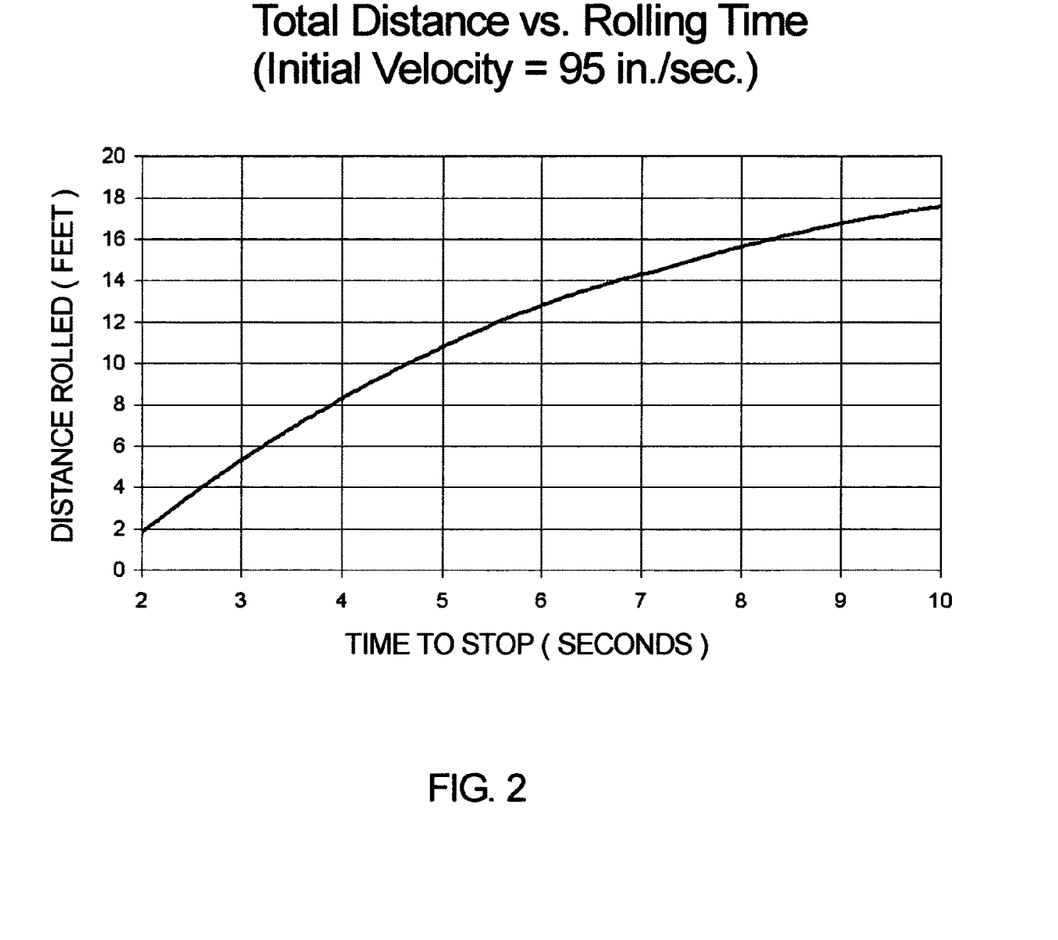
FIG. 2 shows a graph which displays the relationship between the time required for a golf ball to come to a complete stop vs. the total distance rolled were the ball is launched across the surface at a known initial velocity.

FIG. 2 illustrates a plot of the function of distance rolled in feet or equivalent stimp value vs. rolling time to stop when the ball has been launched with an initial velocity of approximately 95 inches per second. This graph covers the range of green speeds that would be encountered on typical golf courses.

Figure 3:
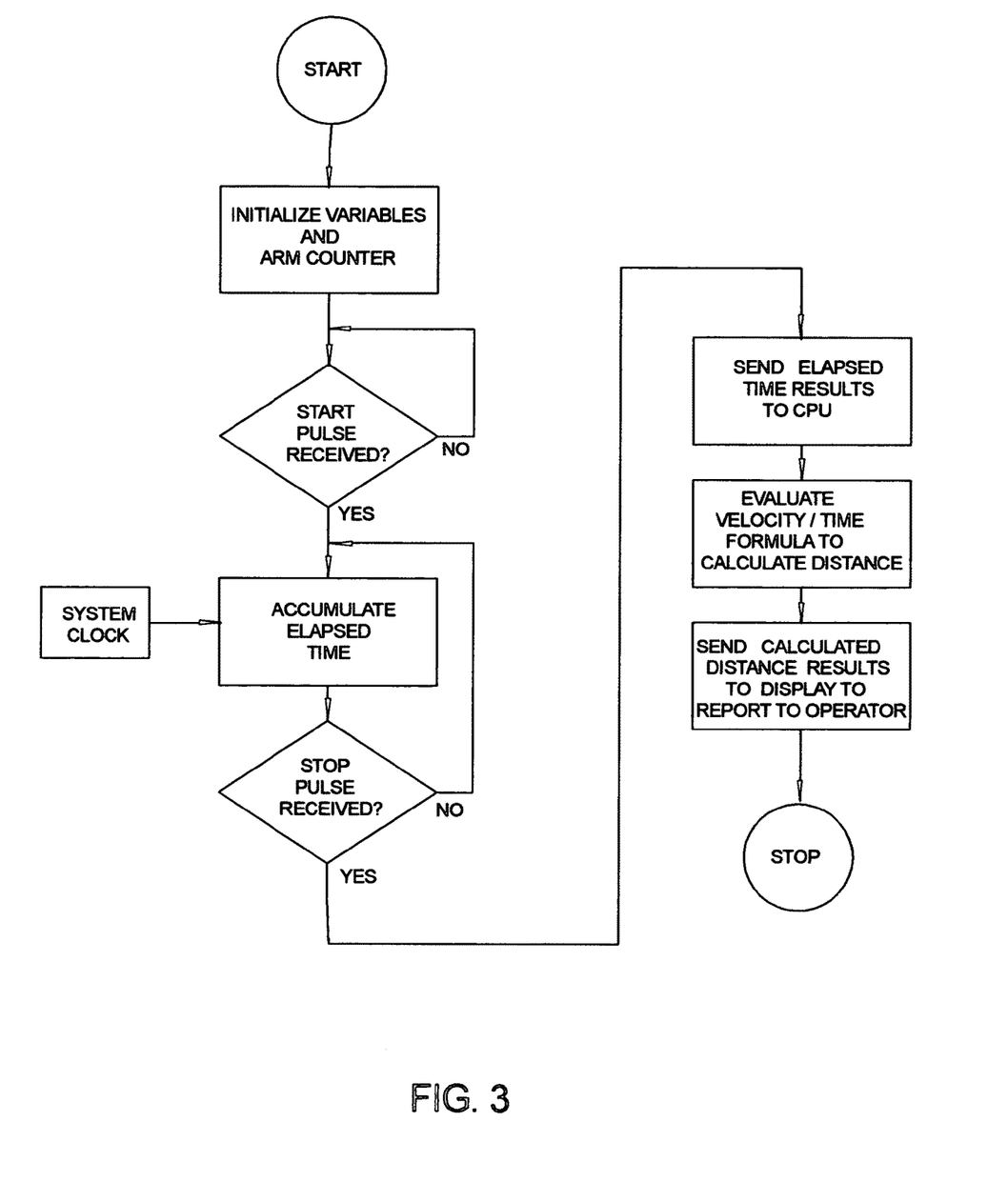
FIG. 3 shows a flowchart outlining the logical operation of the CPU program and the steps performed in obtaining the measurement.

FIG. 3 shows a listing of a flowchart which delineates the sequence of steps that are required to implement the green speed measurement process of the present invention. The Central Processing Unit 26 executes this program.

Figure 4A:
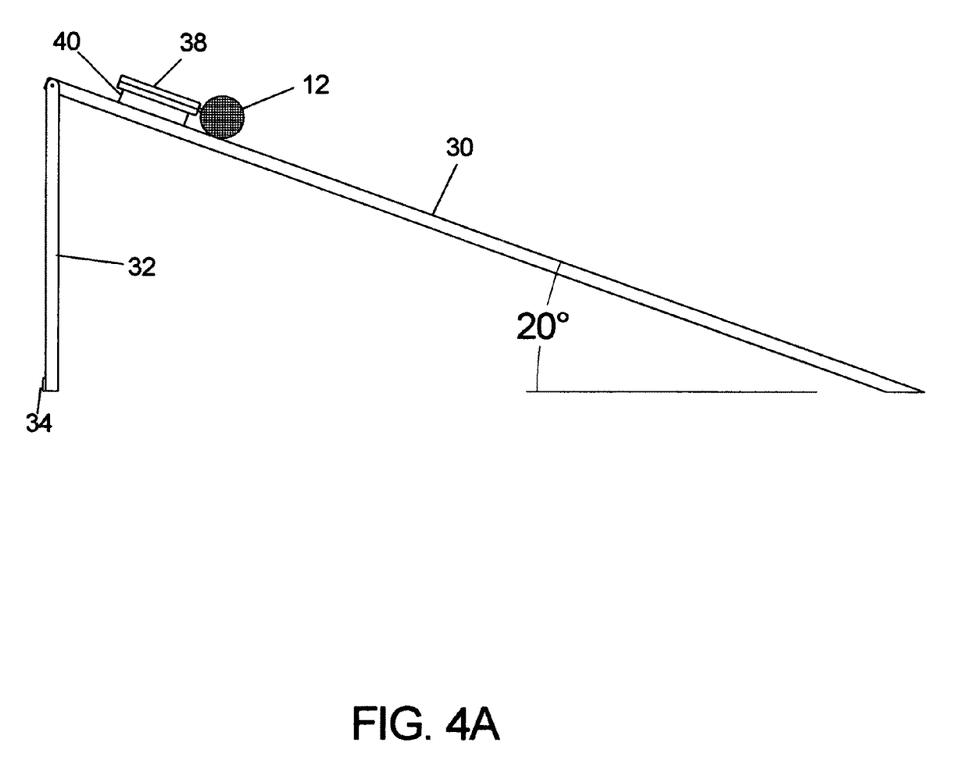
FIG. 4A shows a side view of one embodiment of the present invention where the launching mechanism is a ramp.
Figure 4B:
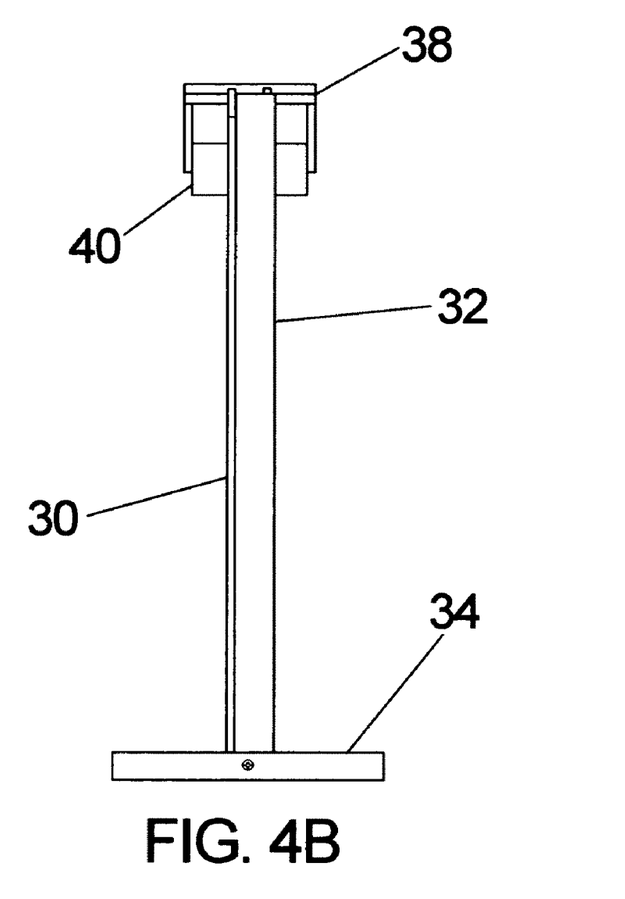
FIG. 4B is a rear view of the ramp embodiment.
Figure 4C:
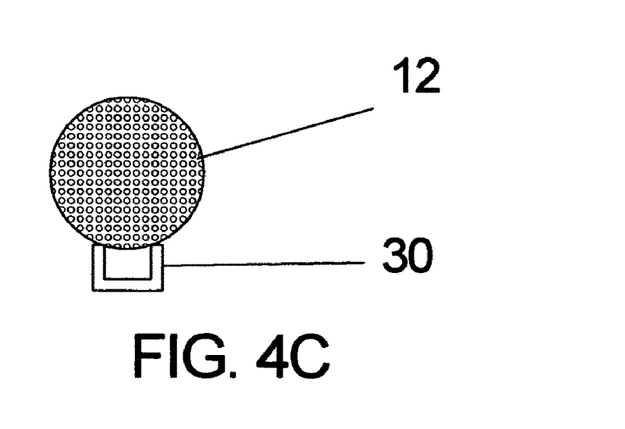
FIG. 4C shows an end view of the embodiment and the relationship of the ball to the supporting rails.

FIGS. 4A through 4D show the first physical embodiment of the present invention. In this embodiment, the means for launching the measuring ball across the horizontal surface 15 to be measured consists of a ramp, the main member of which is the long ball rail 30. The elevated end of ball rail 30 is supported by vertical ball rail support 32. This vertical member elevates the ball rail 30 so that it forms an angle of 20 degrees from the horizontal surface. This insures that the ball release position is at a constant height above the surface so that the ball contains a specific and consistent amount of potential energy before being released. This is then translated into a consistent initial velocity when the ball exits the end of the ramp as the potential energy is converted into kinetic energy by the gravitational force. The electronic control module 38 is mounted on top of spacing block 40 so that the center of the module lines up with the axis of the ball 12. FIG. 4B shows the stabilizing cross member 34 which maintains the ramp assembly in its vertical position so that it is self-supporting for ease of use. FIG. 4C illustrates the relationship between the ball 12 and the sides of the ball rail 30. The ball rests essentially on 2 points separated by 0.5 inches so that only a small amount of friction is exerted on the ball as it rolls down the ramp.

Figure 4D:
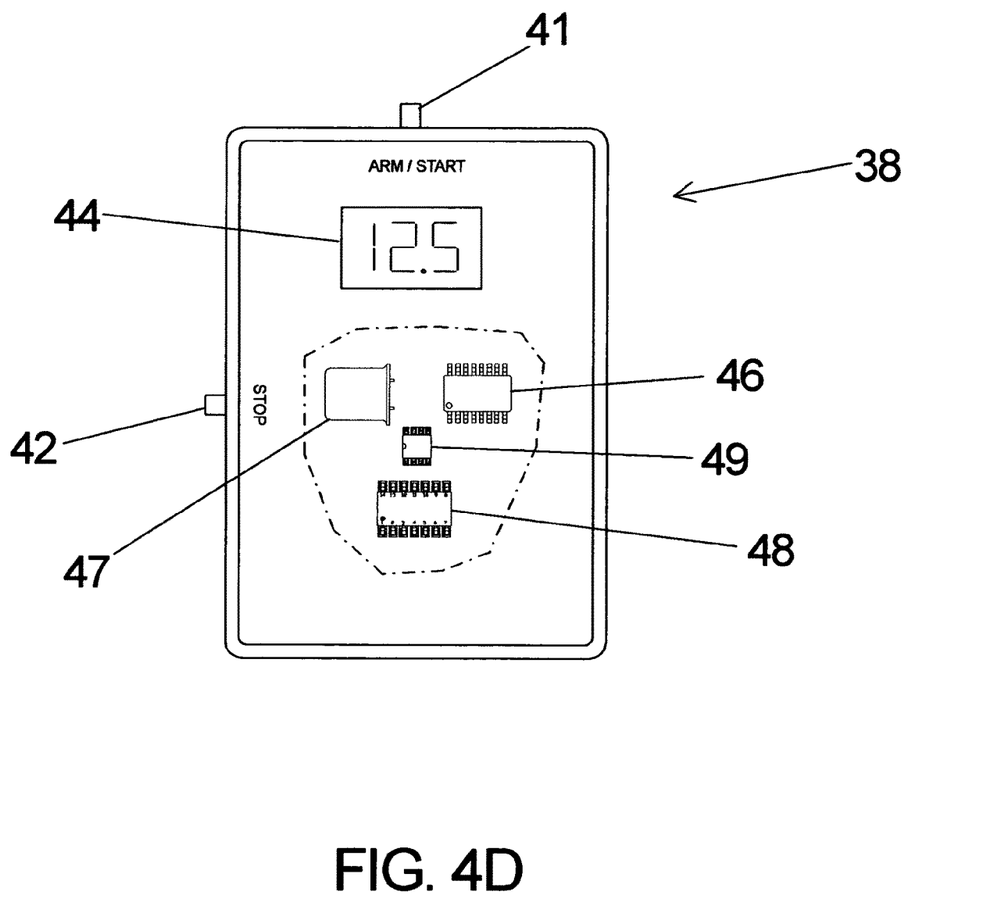
FIG. 4D shows a top view of the electronic timing and control module of the present invention.

FIG. 4D shows the electronic control module 38 which is mounted on the ball rail 30. This module contains the circuitry which implements the measurement process. Start switch 41 is a normally open single pole single throw (NO-SPST) push button switch which arms the timing device when the ball is held in contact, closing the switch. When the ball is released down the ramp to start the measurement, switch 41 opens again which triggers the electronic timing circuit 46 to start counting the elapsed time. Stop switch 42 is also a NO-SPST device which is connected to the electronic timing circuit 46 to terminate the elapsed time counter when activated at the exact time when the measuring ball comes to rest. The electronic timing and control module 38 contains the electronic timing circuit 46 which counts the elapsed time between switch closures and the CPU 48 which determines the results of the measurement and passes them to numeric display 44. Accuracy of the time measurement is assured as the timer is referenced to precision time base 47.

OPERATION

First Embodiment

The operation sequence of the ramp embodiment as illustrated in FIGS. 4A through 4D is as follows:

1. The ramp consisting of ball rail 30 is placed in position on the horizontal surface 15 to be measured with vertical ball rail support 32 in the vertical position supported by stabilizing cross-member 34.
2. The measuring ball 12 is placed on the ramp rails and held against switch 41 closing the switch and arming the measurement.
3. Ball 12 is then released which opens switch 41 and starts the electronic timing circuit 46 to begin the measurement.
4. Ball 12 rolls down ball rail 30 gaining speed as its potential energy is converted to kinetic energy by the force of gravity. Upon reaching the end of the ramp, the ball is launched across the surface at an initial velocity which is consistent for each launching instance.
5. Ball 12 continues to roll across the horizontal surface 15 while its speed decreases steadily. The rate of decrease in velocity or negative acceleration is determined primarily by the coefficient of rolling friction of the surface.
6. Due to the deceleration effects, the ball eventually loses all of its kinetic energy and comes to rest. At the instant when motion ceases, stop switch 42 is closed which signals the electronic timing circuit 46 to terminate the elapsed time measurement.
7. The distance that the ball has rolled may then be calculated since the initial velocity and the elapsed rolling time are now known. When measured in feet, this distance is defined as the "stimp" value of the green. CPU 48 receives the elapsed time data from the electronic timing circuit 46 and determines the equivalent stimp value which corresponds to the measured elapsed time. This may be ascertained by evaluation of a mathematical formula given the constants and current value of the variables or may be established by searching a look-up table of empirically obtained calibration data.
8. Once the stimp value has been determined, the result is communicated to the operator interface which takes the form of numeric display 44 located prominently on the top surface of the control module.

DESCRIPTION

Alternative Embodiment—FIGS. 5A-5D

A further additional embodiment of the present invention is in the form of a compact hand-held device which facilitates a much broader usage of the instrument. While the ramp embodiment as described in FIGS. 4A through 4D provides a precision instrument which may be most often used by green superintendents and other professionals, it is an object of this embodiment to provide a device which is convenient for any golfer to carry and may be quickly used to evaluate current and changing green conditions. The size of this embodiment is reduced to the greatest extent possible given the dimensions of the golf ball and the launching mechanism. This provides for a very compact instrument which may easily be carried in a golfer's pocket or clipped to the golf bag.

Figure 5A:
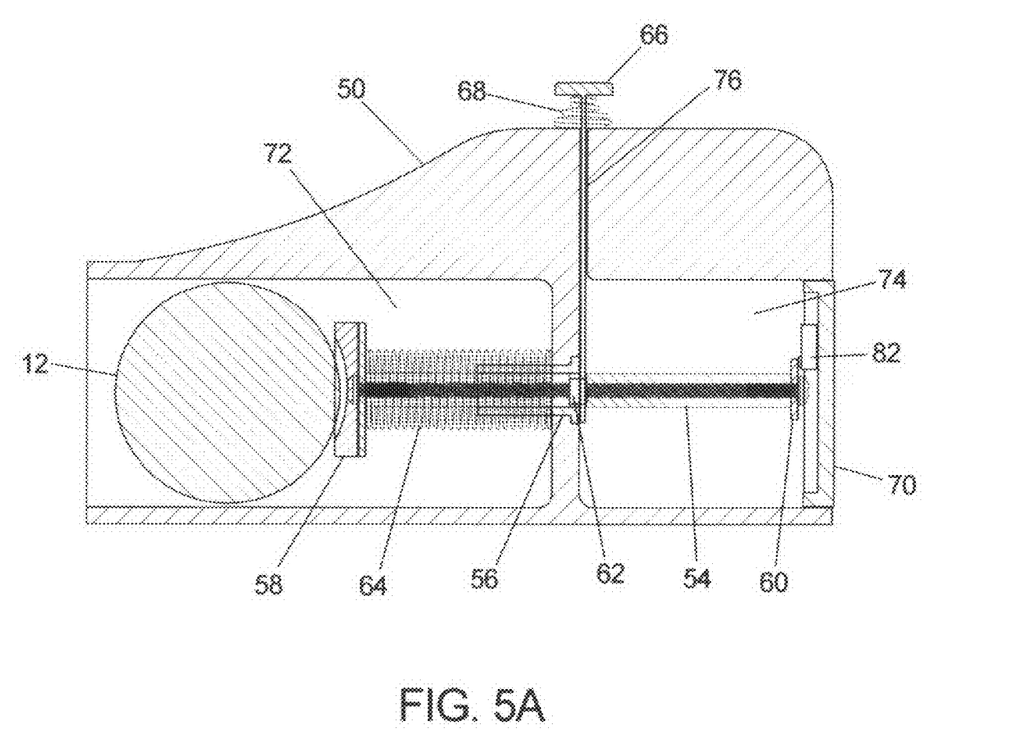
FIG. 5A shows a cross-sectional side view of a hand held embodiment illustrating the internal ball launching mechanism.
Figure 5B:
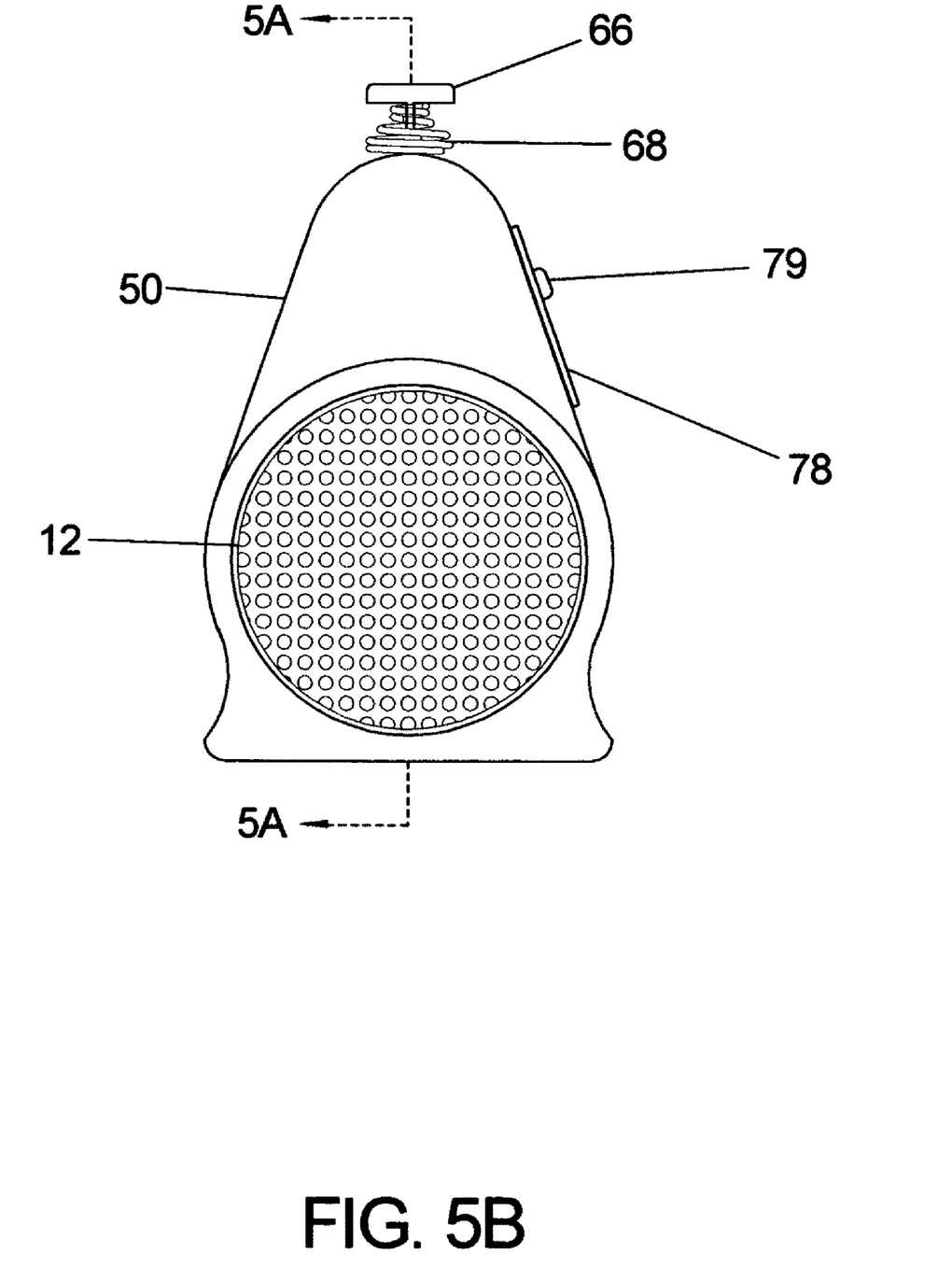
FIG. 5B shows a front view in accordance with the hand held embodiment.
Figure 5C:
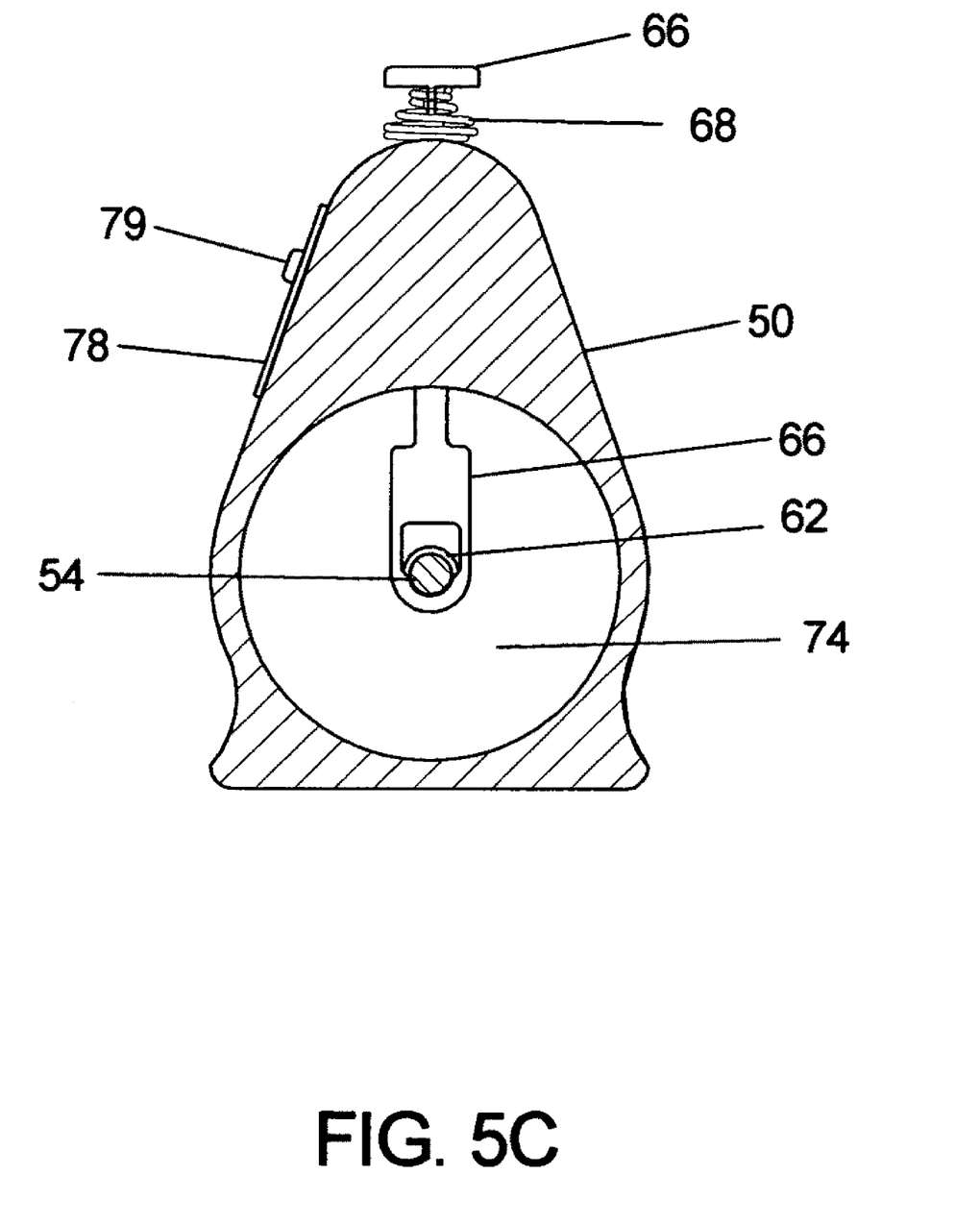
FIG. 5C shows a cross-sectional rear end view of the hand held embodiment.
Figure 5D:
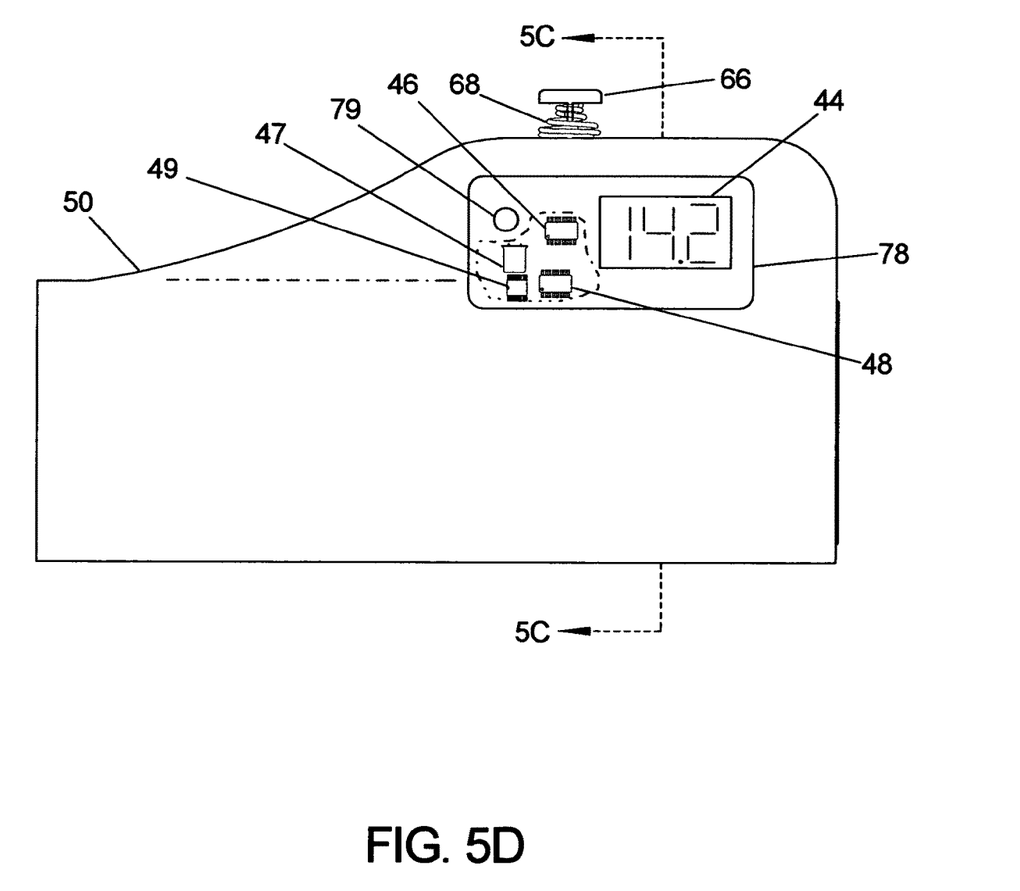
FIG. 5D shows a side view of the hand held embodiment in which the size of the device is reduced to a minimum given the physical constraints of the dimensions of the ball and other mechanical components.

FIG. 5A shows a cross sectional side view of the additional embodiment which illustrates the internal launching mechanism. The hand held body of the device 50 contains key structural elements that have been molded therein. These include: launch cavity 72, rear release cavity 74 and retention bracket slot 76. The measuring ball 12 is launched across the surface to initiate the measurement. The ball plunger shaft 54 slides through bushing bearing 56. The ball contact pad 58 presses against the surface of the measuring ball. The retaining washer 60 prevents the plunger assembly from shooting out of the device. The retention notch 62 holds the plunger assembly in the armed position. The compression spring 64 provides the kinetic energy to propel the ball across the surface to be measured. The spring has a specific spring constant to launch the ball with an initial velocity of approximately 95 inches per second. The retention bracket 66 engages in the retention notch to hold the plunger assembly in the compressed and armed position. Conical spring 68 keeps a positive upward pressure on the retention bracket. Back plug 70 closes off the back of the rear cavity and is removable allowing access to the rear of the plunger assembly. Start switch 82 arms the counter and initiates the timing upon the release of the ball. FIG. 5B is a front view of the embodiment showing the ball 12 in the launch cavity 72. Also shown on the side of the assembly is the electronic timing and control circuit 78 which includes the measurement stop switch 79, the electronic timing circuit 46, the time base 47, the central processing unit 48 and the numeric display 44. FIG. 5C shows a cross-sectional rear view of this embodiment. This figure illustrates how the retention bracket 66 engages with the retention notch 62 to hold the plunger assembly in the armed position.

OPERATION

Alternative Embodiment—FIGS. 5A-5D

A green speed measurement is performed using the alternative embodiment as follows:
1. The measuring ball 12 is inserted into the launch cavity 72 against the ball contact pad 58.
2. The ball is pushed into the cavity moving the plunger shaft 54 into the device, compressing spring 64.
3. The plunger assembly is pushed in until the retention notch 62 reaches the plunger retention bracket 66.
4. The upward force from the conical spring 68 forces the retention bracket up into the notch locking the plunger assembly in the armed position.
5. The body of the green speed measurement device 50 is then placed on the green surface to be measured 15.
6. The device is oriented in the desired direction to be measured. Latch retention bracket 66 is then depressed which releases plunger assembly from the retention notch. This allows the tension of the compression spring 64 to be released propelling the measuring ball across the green surface. Switch 82 is opened by the same action which triggers the electronic timing circuit 46 in the electronic timing and control circuit 78 to begin accumulating the elapsed time.
7. The ball is ejected from the launch cavity 72 at an initial velocity of approximately 95 inches per second.
8. Ball 12 continues to roll across the horizontal surface 15 while its speed decreases steadily. The rate of decrease in velocity or negative acceleration is determined primarily by the coefficient of rolling friction of the surface.
9. Due to the deceleration effects, the ball eventually loses all of its kinetic energy and comes to rest. At the instant when motion ceases, stop switch 79 is closed which signals the electronic timing circuit 46 to terminate the elapsed time measurement.
10. The distance that the ball has rolled may then be calculated since the initial velocity and the elapsed rolling time are now known. CPU 48 receives the elapsed time data from the electronic timing circuit 46 which is referenced to the precision time base 47 and determines the equivalent stimp value which corresponds to the measured elapsed time. This may be ascertained by evaluation of a mathematical formula given the constants and current value of the variables or may be established by searching a look-up table of empirically obtained calibration data.
11. Once the stimp value has been determined, the result is communicated to the operator interface which takes the form of numeric display 44 located prominently on the side surface of the hand held body 50.

DESCRIPTION

Figure 6A:
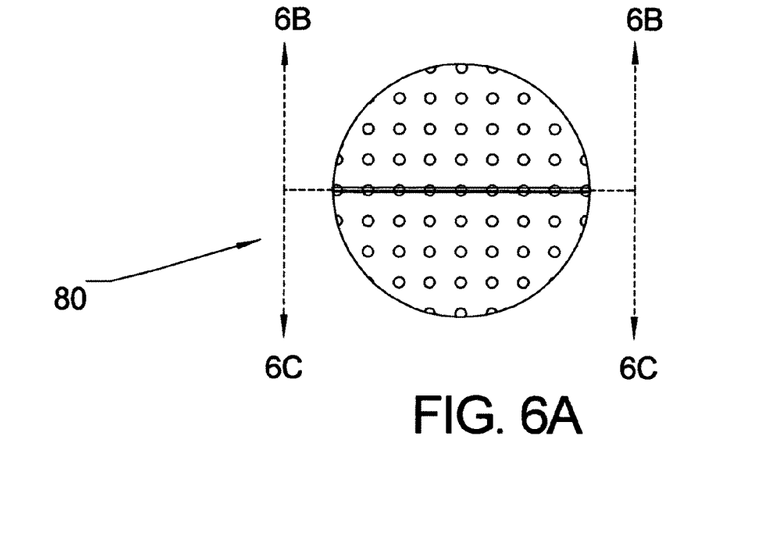
FIG. 6A shows a view of an electronic measuring ball which contains a motion sensing device and means of wireless communication with the timing and control module of the other embodiments.
Figure 6B:
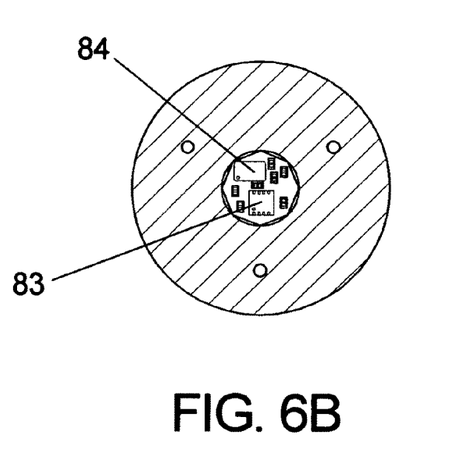
FIG. 6B shows a cross-sectional view of the measuring ball of FIG. 6A illustrating the internal circuit board and the motion sensing and wireless transmission circuitry.
Figure 6C:
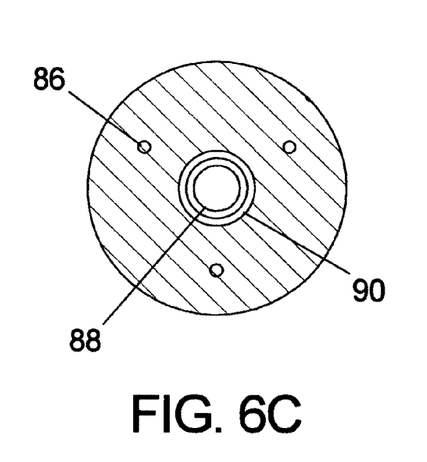
FIG. 6C shows a cross-sectional view of the opposite half of the measuring ball of FIG. 6A illustrating the internal battery location and alignment pins.

Preferred Embodiment—FIGS. 6A-6C

A further preferred embodiment of the present invention utilizes a wireless motion sensing ball 80 as shown in FIG. 6. This ball contains a multi-axis angular rate sensor 83 which produces a signal whenever the ball is in motion in any direction. This sensor 83 is in communication with wireless transmitting circuit 84 which broadcasts a discernable signal indicating that the ball is moving. Battery 88 located in cavity 90 provides power for the device. Alignment pins 86 align the two halves of the ball and secure them when pressed together. This motion sensing ball is used in conjunction with any of the previously described embodiments of the present invention to launch the ball with a consistent initial velocity. This enables the electronic measurement of the green speed to be completely automated requiring no physical action by the operator other than launching the ball across the green surface.

OPERATION

Alternative Embodiment—FIGS. 6A-6C

The wireless motion sensing ball 80 is placed in position on the launching ramp ball rail 30 of FIG. 4 or compressed into the launching cavity 72 of FIG. 5. When the ball is subsequently launched and begins to move, the angular rate sensor 83 generates a signal which is broadcast by the wireless transmitting circuit 84. A wireless receiver circuit 49 in the electronic timing and control module 38 or the electronic timing and control circuit 78 which is tuned to the transmitter frequency receives and detects this signal and triggers the timer to begin counting the elapsed time. The wireless motion sensing ball 80 then rolls across the green surface 15, decelerating until it comes to rest and its motion ceases. Upon the cessation of motion, the signal from the angular rate sensor 83 stops. The transmitted signal from the wireless transmitting circuit 84 expires as well and the exact stopping time is subsequently detected by the wireless receiver circuit 49 in the electronic timing and control module 38 which terminates the electronic timing circuit 46. The total elapsed time from the moment that the wireless motion sensing ball 80 begins to move until it comes to rest is therefore detected autonomously effecting a completely automatic measurement. The resulting elapsed time is then processed by the CPU 48 and the corresponding stimp value is displayed as in the previously described embodiments. This improved device then comprises a very accurate and most convenient method for quickly characterizing the speed of a green surface.

CONCLUSION, RAMIFICATIONS, AND SCOPE

While several different embodiments of the present invention have been described herein, it should be understood that any and all equivalent realizations of the present invention are included within the scope and spirit thereof. The embodiments depicted are presented by way of example only and are not intended as limitations of the present invention. Thus it should be understood by those of ordinary skill in this art that the present invention is not limited to these specific embodi-

What is claimed is:

1. An apparatus for determining the coefficient of rolling friction or relative speed of a horizontal surface said apparatus comprising:
   (a) a measuring ball and means for launching said ball horizontally across a surface at an initial velocity which is substantially constant for each launching instance
   (b) a computing mechanism for controlling a sequence of operations of the apparatus and timing significant events
   (c) a timer for determining the elapsed time between events, said timer incorporating an accurate time base reference
   (d) a sensor to initiate the counting of said timer when the measuring ball has been released
   (e) a sensor inside the ball which terminates the counting sequence of said timer at the instant that the ball ceases rolling and comes to rest
   (f) a central processing unit which processes the measured data to determine the coefficient of rolling friction corresponding to the time interval measured by said timer
   (g) in combination an electronic circuit and means to report the results of the coefficient of rolling friction measurement as determined by said central processing unit.

2. The apparatus of claim 1 wherein the ball launching means consists of a ramp.

3. The apparatus of claim 1 wherein the ball launching means consists of a spring with a specific spring constant.

4. The apparatus of claim 1 wherein the results reporting means consists of an alphanumeric display which is observed by the operator.

5. The apparatus of claim 1 wherein the result reporting means consists of an electronic interface to a further data processing circuit.

6. The apparatus of claim 1 wherein the measuring ball contains motion sensing means for autonomously detecting the motion of the ball or lack thereof.

7. The apparatus of claim 6 wherein the motion detecting measuring ball is in communication with the timer in the control module to autonomously report the instantaneous status of the ball.

8. A method of using the apparatus of claim 1 to determine the coefficient of rolling friction of a surface comprising:
   (a) determining the elapsed time between the time the ball is released and the time the ball comes to rest
   (b) calculating the coefficient of rolling friction for the surface based on the elapsed time and said initial velocity
   (c) reporting the results of step (b) to a display.

* * * * *